US012680540B2

(12) United States Patent
Chen et al.

(10) Patent No.: US 12,680,540 B2
(45) Date of Patent: Jul. 14, 2026

(54) PERISTALTIC PUMP

(71) Applicant: Keurig Green Mountain, Inc.,
Burlington, MA (US)

(72) Inventors: Jiann Chen, Weston, MA (US); Mario Liuzza, Chelmsford, MA (US)

(73) Assignee: Keurig Green Mountain, Inc.,
Burlington, MA (US)

( * ) Notice: Subject to any disclaimer, the term of this patent is extended or adjusted under 35 U.S.C. 154(b) by 0 days.

(21) Appl. No.: 18/881,399

(22) PCT Filed: Jul. 13, 2023

(86) PCT No.: PCT/US2023/027590
§ 371 (c)(1),
(2) Date: Jan. 6, 2025

(87) PCT Pub. No.: WO2024/015489
PCT Pub. Date: Jan. 18, 2024

(65) Prior Publication Data
US 2025/0354545 A1      Nov. 20, 2025

Related U.S. Application Data

(60) Provisional application No. 63/389,175, filed on Jul. 14, 2022.

(51) Int. Cl.
 *F04B 43/12*      (2006.01)
 *A61M 5/142*      (2006.01)
 *A61M 60/279*      (2021.01)

(52) U.S. Cl.
 CPC ..... *F04B 43/1276* (2013.01); *A61M 5/14232* (2013.01); *A61M 60/279* (2021.01);
 (Continued)

(58) Field of Classification Search
 CPC combination set(s) only.
 See application file for complete search history.

(56) References Cited

U.S. PATENT DOCUMENTS

| | | |
|---|---|---|
| 3,447,478 A | 6/1969 | Clemens |
| 3,787,148 A | 1/1974 | Kopf |
| (Continued) | | |

FOREIGN PATENT DOCUMENTS

| | | |
|---|---|---|
| FR | 2 549 909 A1 | 2/1985 |
| FR | 2 716 940 A1 | 9/1995 |
| WO | WO 2024/104051 A1 | 5/2024 |

OTHER PUBLICATIONS

International Search Report and Written Opinion mailed Oct. 27, 2023 for International Application No. PCT/US2023/027590.
(Continued)

*Primary Examiner* — Binh Q Tran
(74) *Attorney, Agent, or Firm* — Wolf, Greenfield & Sacks, P.C.

(57) ABSTRACT

A peristaltic pump can include radially movable lobes (4) to selectively contact a pump conduit (22) to drive fluid flow or permit free flow through the conduit. Lobes can be caused to move radially outwardly to engage a pump conduit in response to forward and reverse drive rotations of the lobes and/or a carrier (3) on which the lobes are mounted. Lobes can be contacted by a drive element (13) to move the lobes radially outwardly and to drive pump operation.

20 Claims, 3 Drawing Sheets

(52) U.S. Cl.
CPC ....... *F04B 43/1215* (2013.01); *F04B 43/1223*
(2013.01); *F04B 43/1253* (2013.01); *F04B*
*43/1261* (2013.01)

(56) References Cited

U.S. PATENT DOCUMENTS

| | | | | | |
|---|---|---|---|---|---|
| 4,142,845 | A | * | 3/1979 | Lepp ........................ | A61M 1/30 |
| | | | | | 251/9 |
| 5,586,872 | A | * | 12/1996 | Skobelev ............ | F04B 43/1276 |
| | | | | | 417/477.8 |
| 6,082,977 | A | | 7/2000 | Nishioka | |
| 7,578,662 | B1 | * | 8/2009 | Ibragimov .......... | F04B 43/1246 |
| | | | | | 417/474 |
| 10,273,950 | B2 | | 4/2019 | Buckberry et al. | |
| 10,744,784 | B2 | | 8/2020 | Yokoi | |
| 2004/0037724 | A1 | * | 2/2004 | Haser .................. | F04B 43/1284 |
| | | | | | 417/477.9 |
| 2005/0095155 | A1 | * | 5/2005 | Blight ................. | A61M 3/0201 |
| | | | | | 417/477.13 |
| 2010/0129247 | A1 | | 5/2010 | Lauer | |
| 2018/0003168 | A1 | | 1/2018 | Yaeguchi et al. | |
| 2018/0230988 | A1 | * | 8/2018 | Fang ................... | F04B 43/0072 |
| 2020/0155744 | A1 | * | 5/2020 | Tsoory ...................... | F04C 5/00 |
| 2020/0263682 | A1 | * | 8/2020 | Imai .................... | F04B 43/1253 |
| 2021/0204528 | A1 | * | 7/2021 | Lindenmoyer ....... | F04B 49/065 |

OTHER PUBLICATIONS

International Preliminary Report on Patentability mailed Jan. 23, 2025 for International Application No. PCT/US2023/027590.

* cited by examiner

PERISTALTIC PUMP

CROSS-REFERENCE TO RELATED APPLICATION

This application is a national stage filing under 35 U.S.C. § 371 of International Application No. PCT/US2023/027590, filed Jul. 13, 2023, which claims the benefit of U.S. Provisional Application No. 63/389,175, filed Jul. 14, 2022. The contents of these applications are incorporated herein by reference in their entirety.

FIELD

This disclosure relates to pumps for moving a fluid.

BACKGROUND

Peristaltic pumps are used in a variety of applications such as food or beverage systems, e.g., fluid transfer applications that benefit from isolation of pumped fluid from the pump components. Some peristaltic pumps work by compressing or squeezing a length of flexible tubing. A mechanical mechanism pinches a portion of the tubing progressively along a length of the tubing and pushes fluid in the tubing in the direction that the tubing is progressively pinched. Rotary peristaltic pumps typically move liquids through flexible tubing placed in an arc-shaped raceway. Multiple rollers placed on a roller carrier are driven rotationally and apply pressure to the flexible tubing to provide a pinching or squeezing action on the tubing. The squeezing or pinching of the tubing creates increased pressure ahead of the squeezed area and recovery or expansion of the tubing creates reduced pressure behind that area, thereby forcing a fluid through the tubing as the roller carrier moves the rollers along the tubing.

SUMMARY

In some embodiments, a peristaltic pump includes a housing defining a cavity configured to hold a flexible pump conduit. For example, the housing can define an arcuate raceway of any suitable arcuate length in which the flexible pump conduit is held. A portion of the housing where the pump conduit is held be a conduit occlusion section where the pump conduit is squeezed or pinched to cause fluid flow through the pump conduit. A carrier can be mounted in the cavity for rotation relative to the housing, and one or more lobes can be mounted for rotation with the carrier. The lobe(s) can be configured to contact and compress the flexible pump conduit against the housing in the conduit occlusion section to cause fluid movement in the flexible pump conduit, e.g., as the lobe(s) and carrier rotate in the housing, the lobe(s) can progressively occlude the pump conduit to cause fluid flow in the conduit. The lobe(s) can be mounted to the carrier for radial movement, e.g., so the lobe(s) can move selectively into and out of contact with the pump conduit in the conduit occlusion section to selectively cause pumping action with the conduit.

In some embodiments, a drive motor can be configured to rotate the carrier and lobe(s) in a first direction and a second direction opposite the first direction, e.g., clockwise and counterclockwise, and the carrier and lobe can be configured to move the lobe from a radially retracted position to a radially extended position in response to rotation of the carrier and lobe by the drive motor in both the first direction and the second direction. For example, in some cases the drive motor can be coupled to the carrier to rotate the carrier in the housing. In response, one or more lobes can move radially outwardly relative to the carrier to contact the pump conduit and cause pumping action through the pump conduit, e.g., by progressively pinching the pump conduit along its length in a conduit occlusion section of the pump. Such radial outward movement can occur both when the carrier is rotated in the first direction and the second direction, e.g., the pump can be reversibly operated to pump fluid through the pump conduit in two opposed directions.

In some embodiments, a drive motor can be configured to contact the one or more lobes to move the lobe radially outwardly to contact the flexible pump conduit and to rotate the lobe and carrier about a drive axis to cause the fluid movement in the flexible pump conduit. Thus, in some cases rotation of the carrier can be caused by rotating one or more lobes, e.g., by arranging the drive motor to have lobe engagement elements contact the one or more lobes to move them radially outwardly relative to the carrier and to rotate in the first and/or second direction. This feature can be combined with the feature that the lobe(s) can be moved radially outwardly in response to rotation of the carrier and/or lobe(s) in both first and second directions, or can be employed independently. For example, a pump can be configured with the drive motor arranged to contact the one or more lobes to move the lobe(s) radially outwardly and rotate the lobe(s) and carrier about a drive axis, e.g., in a first direction, but not be capable of rotation in the second direction, or if rotatable in the second direction, the lobe(s) need not be configured to move radially outwardly in response to rotation in the second direction. Alternately, the drive motor can be arranged to contact the one or more lobes to move the lobe(s) radially outwardly and rotate the lobe(s) and carrier in both first and second directions.

In some cases, the one or more lobes can be selectively moved to a radially inward position, e.g., when positioned in a conduit occlusion section, so that the pump conduit is not fully pinched or occluded by the lobe(s). In this free flow state, fluid can flow through the pump conduit, e.g., due to gravity, a siphon, a separate pump, etc. In some cases, the free flow state can be achieved by momentarily rotating the lobe(s) and/or carrier and/or a drive element in a reverse direction so as to cause the lobe(s) to move radially inwardly relative to the carrier. For example, the pump may be initially operated so the carrier and lobe(s) are rotated clockwise. To put the pump in a free flow state, the carrier and/or lobe(s) can be briefly rotated counterclockwise to move the lobe(s) radially inwardly, particularly lobe(s) that are in a conduit occlusion section of the pump.

In some embodiments, the carrier can include a slot and a lobe can be configured to move radially outwardly relative to the carrier along the slot. For example, the carrier can include one or more plates that includes a slot, e.g., that defines a type of cam surface. The slot can extend, at least in part, in a radial direction on the carrier. For example, the slot can have an arcuate shape such that one portion of the arcuate shape is positioned radially inward relative to another portion of the arcuate shape. A lobe can ride along the slot, e.g., in a way similar to a cam follower riding along a cam surface. Movement of the lobe along the slot can cause the lobe to move radially inwardly and outwardly relative to the carrier. In some cases, the carrier can include first and second drive plates coupled to the drive motor, and each of the first and second drive plates can include first and second slots respectively. Each lobe can include a roller having first and second opposed ends respectively engaged with first and second slots of the first and second drive plates and configured for movement along the first and second slots. For example, each lobe can have a pivot axis about which the lobe is rotatable relative to the carrier. The pivot axis, which can be configured as an axle on which a roller element can rotate, can be configured to move along a slot or other guideway on the carrier. Thus, each lobe can be configured as a tube roller that is positioned between first and second drive plates of the carrier and has ends that move along respective slots of the first and second drive plates and thereby move the roller radially inwardly and outwardly. In some cases, a slot can include a pair of curved portions that meet at a junction and respectively extend from the junction in a radially outward direction. For example, the pair of curved portions can form a "V" shape, e.g., with the junction between the curved portions located at a radially inwardmost part of the slot. Portions of the slot that extend from the junction can be arranged to position the lobe at radially outward locations relative to the junction. As noted above, in some cases the drive motor can be configured to rotate the carrier, which causes the one or more lobes to rotate with the carrier and move radially outwardly or inwardly relative to the carrier by movement along a slot.

In some embodiments, the drive motor can be configured to rotate the one or more lobes (e.g., in first and/or second directions), which causes the carrier to rotate and the one or more lobes to move radially outwardly or inwardly. For example, a drive element can be coupled for rotation by the drive motor, and the drive element can be configured to contact the one or more lobes to drive the lobe(s) to rotate in the first and/or second directions. As an example, the drive element can include a drive roller that is configured to contact a lobe (e.g., configured as a roller, and sometimes referred to as a tube roller to distinguish from the drive roller) to cause the lobe to rotate in the first direction and move radially outwardly. The drive element can be mounted for rotation about a drive axis (e.g., an axis about which the shaft of a drive motor rotates), and the drive element can cause the lobe(s) to rotate in the first direction about the drive axis. A drive element configured as a drive roller can rotate about the drive axis as well as a drive roller axis that is spaced from the drive axis, e.g., the drive roller can rotate about its own axis as well as the drive axis of the motor. A lobe configured as a tube roller can rotate about the drive axis as well as a tube roller axis that is spaced from the drive axis and the drive roller axis. In some cases, the drive element can include a plurality of drive rollers configured for rotation about the drive axis, and the lobe(s) can include a plurality of tube rollers mounted for rotation with the carrier in the first and/or second directions about the drive axis. Each drive roller can be configured to contact a first tube roller to cause the first tube roller to rotate in the first direction and move radially outwardly in response to rotation of the drive roller about the drive axis in the first direction, and configured to contact a second tube roller to cause the second tube roller to rotate about the drive axis in the second direction and move radially outwardly in response to rotation of the drive roller about the drive axis in the second direction.

In some cases, the drive element can include a lobe-engagement element that includes a cam with a cam surface configured to contact a lobe. As an example, the cam can be mounted to a drive shaft of the drive motor and include one or more angled or sloped cam surfaces configured to engage a respective lobe and move the lobe radially outwardly for at least one direction of rotation of the cam. The engagement of the cam with the lobe can also cause rotation of the lobe and associated carrier about the drive axis. In some cases, a lobe can include a tube roller configured to rotate about a tube roller axis relative to the carrier, and the tube roller can be pivotally mounted on a carriage that is slidably mounted to the carrier. A cam surface of the cam can be configured to contact the carriage and move the carriage and tube roller radially outwardly as well as cause the carriage and tube roller to rotate about the drive axis.

These and other aspects of the disclosure will be apparent from the following description and claims. It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

In the drawings, each identical or nearly identical component that is illustrated in various figures may be represented by a like numeral. For purposes of clarity, not every component may be labeled in every drawing. In the drawings.

DETAILED DESCRIPTION

It should be understood that aspects of the disclosure are described herein with reference to certain illustrative embodiments and the figures. The illustrative embodiments described herein are not necessarily intended to show all aspects of the disclosure, but rather are used to describe a few illustrative embodiments. Thus, aspects of the disclosure are not intended to be construed narrowly in view of the illustrative embodiments. In addition, aspects of the disclosure may be used alone or in any suitable combination with other aspects of the disclosure. For example, embodiments are described in which rotation of a drive element causes the drive element to contact lobes of a pump to cause the lobes to move radially outwardly as well as drive operation of the pump for fluid movement. Embodiments are also described in which operation of the pump in two different rotation directions (e.g., forward and reverse) causes pump lobes to move radially outwardly. These two features can be employed together in a pump, or can be used separately and without the other. To the extent not mutually exclusive, other features described herein can be employed together or separately in various embodiments.

Peristaltic pumps can be used for a variety of different applications, and embodiments described herein are not limited to any particular use. For example, pumps described herein can be used to drive fluid flow in a beverage machine, e.g., to move water to and through a heater and to a chamber where water is mixed with beverage material to form a beverage such as coffee, tea or an otherwise flavored beverage. Pumps can also be used to provide metered doses liquid material, such as a flavoring or other additive for a beverage, a drug or other therapeutic, and so on. In short, pumps of this disclosure should not be construed as limited to any particular pump application.

In some embodiments, a peristaltic pump can be arranged so that driving of the pump in two directions (e.g., forward and reverse) can cause one or more lobes to move radially outwardly to contact a flexible pump conduit and cause fluid movement in the flexible conduit. In some cases, the one or more lobes can have a radially extended position such as where a lobe contacts a pump conduit to fully pinch or otherwise occlude the pump conduit to prevent flow through the occluded conduit portion and a radially retracted position, e.g., in which a lobe does not occlude the pump conduit and can allow flow through the pump conduit. In some embodiments, the pump can have a pump conduit occlusion section where lobes can move radially to occlude the pump conduit based on pump drive rotation. In the absence of pump drive rotation, lobes within the pump conduit occlusion section can be moved radially inwardly to permit flow through the pump conduit. This configuration can permit siphon flow or other unrestricted flow through the pump as desired.

Figure 1:
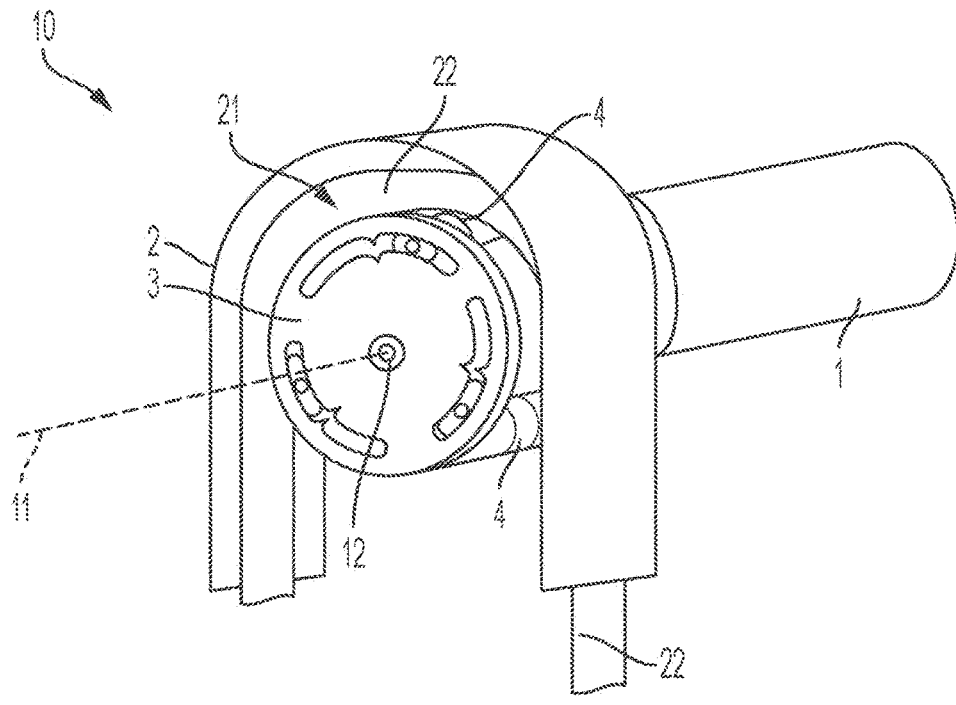
FIG. 1 is a perspective view of a peristaltic pump in an illustrative embodiment.
Figure 2:
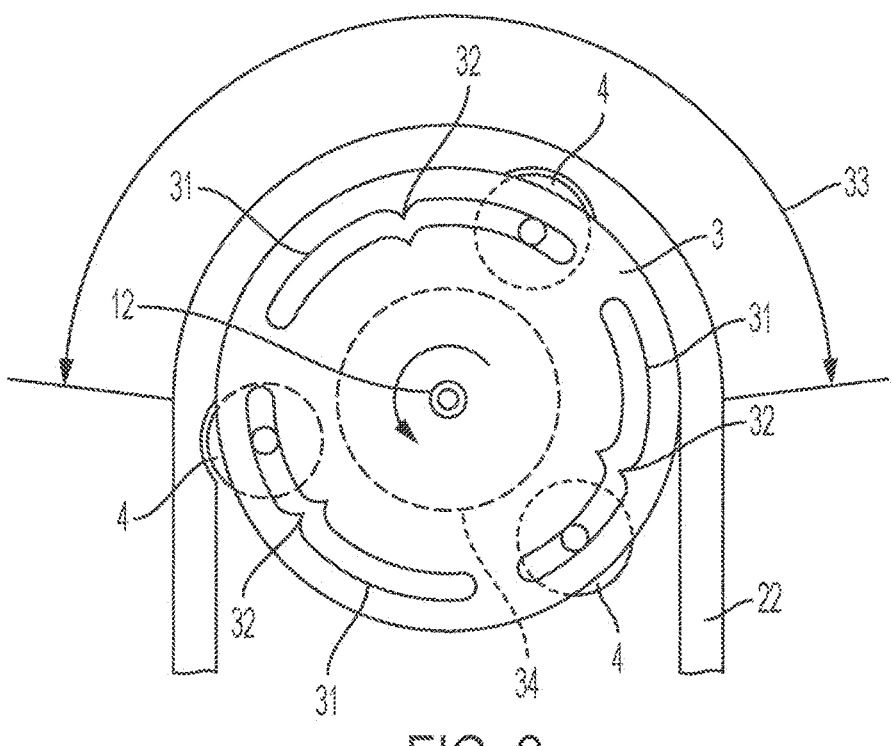
FIG. 2 is a front view of a carrier and lobe arrangement in the FIG. 1 pump.
Figure 3:
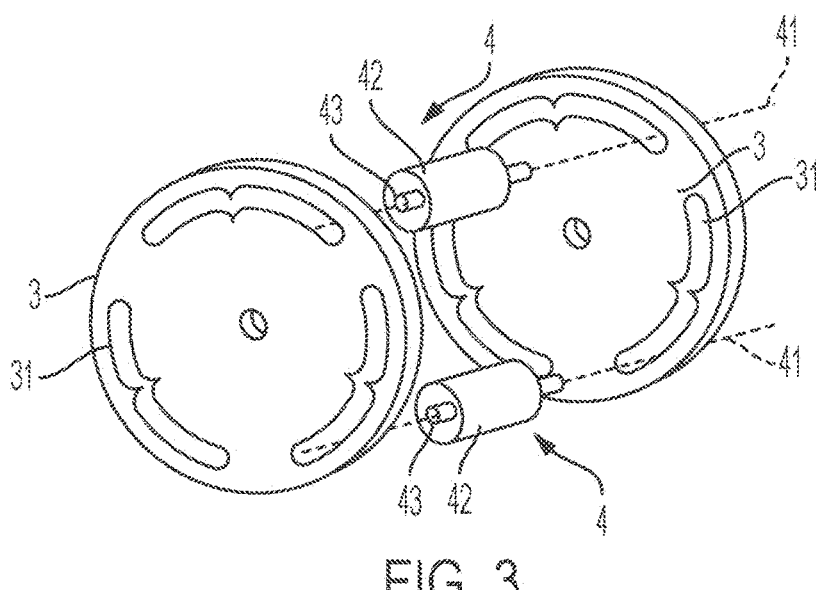
FIG. 3 is an exploded view of the carrier and lobe arrangement of FIG. 2.

FIGS. 1-3 show an illustrative embodiment of a peristaltic pump 10 that includes a drive motor 1 to drive rotation of pump components to cause fluid movement through a flexible pump conduit 22 of the pump 10. The motor 1 can be any suitable drive, such as an electric motor, pneumatic motor, hydraulic motor, etc. The pump 10 includes a housing 2 that defines a cavity 21 in which at least a portion of the flexible pump conduit 22 is held. A carrier 3 is mounted in the cavity 21 for rotation relative to the housing 2, e.g., in clockwise and/or counterclockwise directions about a drive axis 11. The drive axis 11 can be an axis about which a drive shaft 12 of the drive motor 1 rotates, or can be spaced from a rotation axis of the drive motor 1. In some cases, the carrier 3 can be mounted on a drive shaft 12 of the motor 1. In some cases, the carrier 3 can be mounted to the housing 2 or other component for rotation, e.g., the carrier 3 can be mounted on one or more bearings or other components of the housing 2 for rotation and be coupled to the drive shaft 12 (e.g., by one or more gears or other drive train) so the carrier 3 can be rotated by the motor 1. One or more lobes 4 can be mounted for rotation with the carrier 3 and configured to contact and compress the flexible pump conduit 22 against the housing 2 to cause fluid movement in the flexible pump conduit 22. For example, one or more lobes 4 can be arranged to move relative to a portion of the housing 2 (such as a raceway in which the flexible conduit 22 is held) so that the flexible pump conduit 22 can be pinched or otherwise occluded between the lobe 4 and the housing 2. As will be understood, movement of the lobe 4 relative to the housing 4 can occlude the flexible pump conduit 22 so that the occluded section moves along a length of the conduit 22 as the lobe 4 moves, thereby causing fluid movement along the conduit 22.

In some cases, the one or more lobes 4 can be being mounted to the carrier 3 for radial movement relative to the carrier 3. Thus, in some cases the lobes 4 can move toward and/or away from the housing 2 in a conduit occlusion section 33 (or working section) so that the lobes 4 can completely or partially occlude the pump conduit 22 or not occlude the pump conduit 22 at all. As an example, in FIG. 1 the flexible pump conduit 22 extends through the cavity 21 along an approximately 180 degree arc relative to the drive axis 11. (It should be understood, however, that the pump conduit 22 can extend through any suitable arc length in a pump housing.) In at least a portion of the area of the cavity 21 where the pump conduit 22 extends, one or more lobes 4 can be radially moved outwardly to at least partially occlude the pump conduit 22 and cause fluid flow in the conduit 22. This is a conduit occlusion section 33 of the pump 10 as can be seen in FIG. 2, and in some embodiments one or more lobes 4 can be put in a radially retracted position where the lobes 4 do not contact the pump conduit 22 or only partially occlude the conduit 22 in the conduit occlusion section 33. This can allow for free fluid flow through the pump conduit 22 in some cases, e.g., for enabling siphon flow or flow through the pump conduit 22 driven by another pump, gravity, etc.

In some cases, rotation of the one or more lobes 4 and/or carrier 3 can cause the lobe(s) 4 to move radially outwardly, e.g., to occlude the pump conduit 22 in a conduit occlusion section 33 of the pump 1. Also, in some embodiments, rotation of the lobe(s) 4 and/or carrier 3 in two opposite directions, such as clockwise and counterclockwise, can cause the lobe(s) 4 to move radially outwardly at least in a conduit occlusion section 33. For example, in the FIG. 1 embodiment the carrier 3 and lobes 4 are configured so that the lobes 4 move radially outwardly for both rotation directions about the drive axis 11. Thus, the lobes 4 are configured to move from a radially retracted position to a radially extended position at least in a conduit occlusion section 33 in response to rotation of the carrier 3 and lobe 4 by the drive motor 1 in both a first direction and a second direction. Therefore, in some cases the FIG. 1 pump 10 can operate to pump fluid through the pump conduit 22 in one direction for clockwise rotation of the carrier 3 and lobes 4, and pump fluid in a second opposite direction for counterclockwise rotation of the carrier and lobes 4. In addition to being reversibly operable for pumping fluids, the pump 10 can be put in a free flow state where the lobes 4 do not completely occlude the pump conduit 22 so that flow is permitted through the pump conduit 22 from an inlet to an outlet (or vice versa).

FIGS. 2 and 3 show more detailed views of the pump 10 to illustrate how in at least some embodiments the pump 10 can be reversibly operable, and optionally can have a non-occlusion or free flow state in which flow is freely permitted through the pump conduit 22. In some embodiments, the carrier 3 includes two plates that each include slots 31 that engage with a corresponding lobe 4 positioned between the plates. The slots 31 are configured so that as a lobe 4 moves along a slot 31, the lobe 4 moves radially inwardly or outwardly. In some embodiments such as that in FIGS. 1-3, the slots 31 can include a pair of curved portions that meet at a junction 32 and respectively extend outwardly from the junction 32. Each portion of the slot 31 can be arranged so that the slot portion extends at least partially radially outwardly from the junction 32, which may be the radially innermost part of the slot 31. Thus, as a lobe 4 moves along a slot 31 away from the junction 32, the lobe 4 can move radially outwardly (e.g., and toward the pump conduit 22 in a conduit occlusion section 33). In some cases, the pair of curved portions of each slot 31 can form an "V" shape, including a "V" shape in which the ends of the V curve back on themselves. However, the slots 31 can be arranged in other ways, e.g., the slots 31 can be linear and extend in a radial direction on the carrier 3, can be curved and have a "U" or "M" shape with the junction 32 at a bottom of the "U" or "M", and so on.

In some cases, the drive motor can be configured to rotate the carrier to cause the lobe(s) to rotate with the carrier and thereby cause the lobe(s) to move radially outwardly relative to the carrier. For example, in some embodiments the drive motor 1 can rotate the carrier plates 3 by way of a drive shaft 12. The carrier plates 3 can be fixed relative to each other, e.g., by a bushing or other element that extends between the plates, and can be fixed relative to the drive shaft 12. Rotation of the carrier plates 3 will cause the lobes 4 to rotate with the carrier plates 3 and tend to move the lobes 4 along the slot 31 away from the junction 32, e.g., due to inertia and/or frictional contact of the lobes 4 with the pump conduit 22. For example, friction between a lobe 4 and the pump conduit 22 and/or inertia will tend to cause a lobe 4 to move into a "trailing" portion of the slot 31 relative to the direction of rotation of the carrier 3. With increased frictional contact of a lobe 4 with the pump conduit 22, particularly in the conduit occlusion section 33, the lobe 4 may be caused to move further outwardly along the slot 31 and away from the junction 32. This can urge the lobe 4 more forcefully against the pump conduit 22 in the conduit occlusion section 33, and thereby occlude the pump conduit 22 and cause fluid flow in the conduit 22 as the lobe 4 moves relative to the pump conduit 22. In some cases, a lobe 4 can include a pivot axis 41 (see FIG. 3) about which the lobe 4 is rotatable relative to the carrier 3, and the pivot axis 41 can be configured to move along the slot 31. For example, each lobe 4 can be configured as a roller having first and second opposed ends respectively engaged with slots 31 of the carrier plates 3 and configured for movement along the slots 31 based on rotation of the carrier plates 3. Each roller can have a tube roller portion 42 and an axle 43. The axle 43 can be configured to rotate relative to the roller portion 42, e.g., so that the axle 43 remains stationary relative to the slot 31 while the roller portion 42 rotates on the axle 43. This can reduce wear on the slot 31 and axle 43 as well as between the roller portion 42 and the pump conduit 22.

In some cases, a resilient element such as a resilient rubber component or spring can be configured to bias the lobes 4 away from the junction 32 of each slot 31. As an example, a rubber sleeve or ring 34 (see FIG. 2) can be positioned around the drive axis 11 and in a space between the rollers 42 so that the rollers 42 are biased radially outwardly by the sleeve or ring 34, at least when the lobes 4 are positioned at the junction 32. This can be helpful, for example, where the carrier 3 and lobes 4 are configured so that lobes 4 do not contact the pump conduit 22 or contact the pump conduit 22 relatively gently in the conduit occlusion section 33 when the lobe 4 is positioned at the junction 32. The resilient element 34 can help urge a lobe 4 to move away from the junction 32 and into suitable contact with the pump conduit 22 or other component to help move the lobe 4 along the slot 31 and away from the junction 32, e.g., as the carrier 3 is rotated. Once a lobe 4 suitably contacts the pump conduit 22, friction between the lobe 4 and pump conduit 22 can cause the lobe 4 to continue radially outward movement along a slot 31 and the lobe 4 can move out of contact with the resilient element 34 (or not).

In some embodiments, to move the lobes 4 radially inward and to a free flow state, driving of the lobes 4 and/or carrier 3 can simply be stopped. Stopped movement of the carrier 3 and lobes 4 can permit the lobes to move radially inwardly along a respective slot 31, e.g., due to resilient force of the pump conduit 22 on the lobe 4, a resilient element urging the lobe 4 to move radially inwardly, pressure in the pump conduit 22, etc. In some cases, at least lobes 4 in the conduit occlusion section 33 can be moved radially inwardly to a free flow state by momentarily reversing rotation of the carrier 3 and/or lobe 4. For example, in the FIG. 1 embodiment, momentarily reversing rotation of the carrier 3 can cause the lobes 4 (at least those in the conduit occlusion section 33) to move along the slot 31 toward the junction 32. This radially inward movement of the lobe(s) 4 can cause the lobe(s) 4 to reduce a contact force on the pump conduit 22 and open the conduit 22 for free flow. In other embodiments described more below, one or more lobes 4 may be contacted (e.g., by a drive element of the motor 1) to move the lobes 4 relative to the carrier 3 and thus radially inwardly. During such movement, the carrier 3 may remain stationary or move a limited amount suitable to permit the lobe(s) 4 to move radially inwardly relative to the carrier 3. This configuration can provide a convenient way for operating a pump 10 to move fluid and then enter a free flow state to permit flow through the pump 10. For example, a drive motor 1 may rotate a carrier clockwise to pump a fluid through the pump conduit 22 and then momentarily drive the carrier 3 counterclockwise to disengage one or more lobes 4 from the pump conduit 22 sufficiently to permit free flow through the conduit 22. In some embodiments, the pump conduit 22 and/or housing 2 can be rotated relative to the carrier 3 and lobe(s) 4 to cause the lobe(s) 4 to suitably disengage from the pump conduit 22 to permit free flow in the conduit 22. For example, the carrier 3 and lobe(s) 4 can be held stationary and the housing 2 and conduit 22 can be rotated so as to cause the lobe(s) 4 to move along a slot 31 to a radially inward position. Such rotation of the housing 2 and conduit 22 can be in a same direction as the carrier 3 and lobe(s) 4 were previously rotating when causing pumping action, e.g., if the carrier 3 and lobe(s) 4 were rotating clockwise and then stopped, the housing and/or pump conduit 22 can be rotated clockwise to cause the lobe(s) 4 to suitably disengage from the pump conduit 22. This rotation of the housing 2 and/or pump conduit 22 can be caused by a spring or other resilient element, a motor or other actuator, and/or by manually moving the housing 2 and/or conduit 22.

Figure 4:
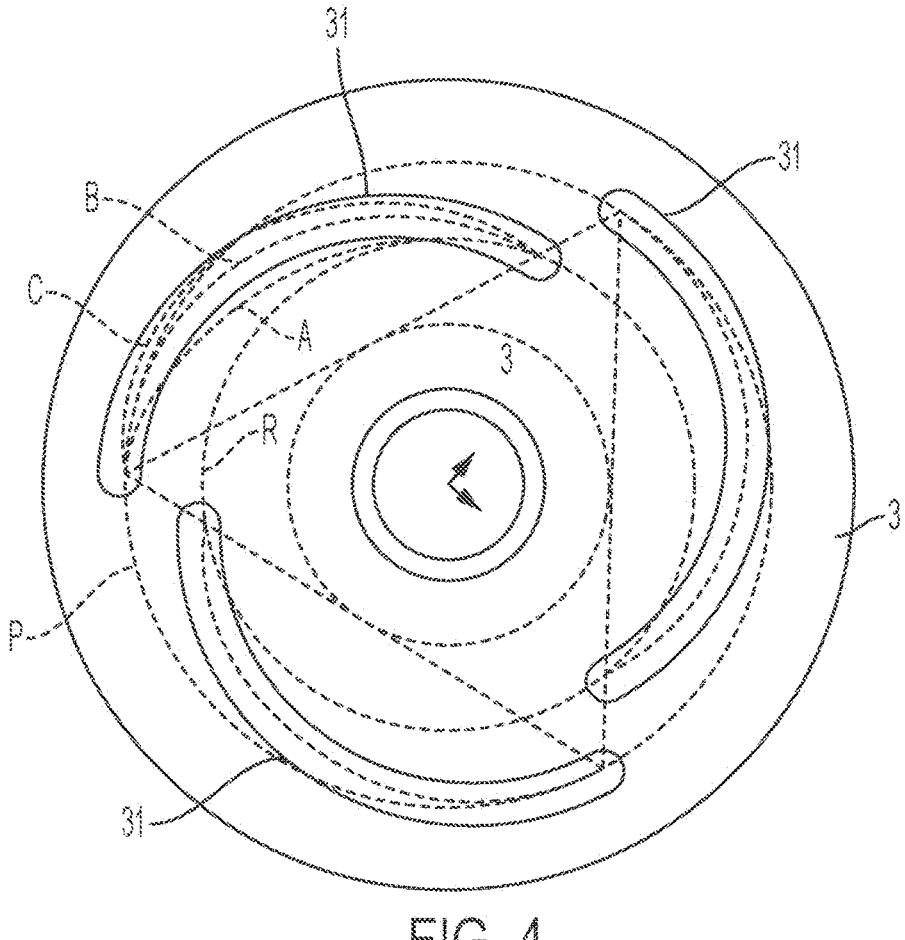
FIG. 4 shows a schematic diagram of a carrier along with alternate slot arrangements.

FIG. 4 shows a schematic view of a carrier 3 with alternate slot paths that may be employed and which illustrate some of the considerations for configuring slots 31 for guiding movement of lobes 4. In the examples of FIG. 4, there are three alternative paths A, B and C for slots 31 each for guiding a respective lobe 4, e.g., in a configuration like that in FIGS. 1-3 although other arrangements are possible. FIG. 4 shows a radial position R (illustrated as a circular line) which in this example corresponds to a lobe 4 position in which the lobe 4 is out of contact with the pump conduit 22 or otherwise engages with the conduit 22 to permit free flow through the pump conduit 22. A radial position P corresponds to a lobe position in which the lobe 4 suitably contacts the pump conduit 22 to occlude the conduit 22 to cause flow through the conduit 22 during pump operation. Arcuate paths A, B and C illustrate three slot 31 arrangements or paths for guiding a lobe 4 from a position R to a position P. Arcuate path B has a slot 31 drawn that corresponds to the path B, e.g., the slot 31 has sides that are equidistant from the path B from a start at position R to an end at position P. The path B continuously moves radially outwardly from the position R to the position P and provides a maximum compression of the lobe on the pump conduit 22 at the radially outermost end of the slot 31 at position P. This slot arrangement corresponding to path B may be suitable for slots 31 having a single arcuate segment that extends radially outwardly from a radially inwardmost position, e.g., at the radial position R. That is, path B may be suitable for pump arrangements configured to pump fluid for only one direction of rotation. The slot path B may provide an arrangement in which the lobe 4 remains at position P even when the carrier 3 and/or lobe 4 rotation is stopped. In contrast, the slot path A has a larger radius of curvature than the path B and may provide an arrangement in which the lobe 4 disengages or moves from the position P when the pump operation is stopped. This is because a slot 31 following path A will present less friction or other resistance to maintain a lobe at the position P, which may move radially inwardly due to force of the pump conduit 22 on the lobe 4 when rotation is stopped. Thus, the path A may provide an arrangement suitable for pump conditions where it is desirable to have the pump provide a free flow state when the pump is stopped. In contrast to paths A and B, path C is configured to have a smaller radius of curvature and to have a portion of the path C extend radially outward of the position line P at locations between the extreme ends of the path C. This arrangement will provide a maximum compression of the pump conduit 22 by the lobe 4 before the lobe 4 reaches the extreme radially outer end of the slot 31 and a slightly smaller compression of the pump conduit 22 at the extreme outer end of the slot 31. Thus, path C may provide an arrangement in which the lobe 4 tends to remain in a position to occlude the pump conduit 22 after pump operation has stopped, and may require the pump to be reversed to disengage the lobe 4 from the pump conduit 22 to provide a free flow state. Configurations like that for path C may be suitable for slots 31 having two slot portions that extend radially outwardly from a radially innermost junction 32, e.g., like that in FIGS. 1-3, because the slot 31 may have a longer compression zone segment where the lobe 4 suitably occludes the pump conduit 22 for causing fluid flow and thereby account for backlash in the drive mechanism. A pair of slot portions having a shape like path C can be used to form a slot 31 that has a "V" shape, including a "V" shape in which the ends of the V curve back on themselves so that extreme ends of the V are positioned radially inwardly from portions of the V near but not at the extreme ends of the slot 31. Path C in FIG. 4 has these features at the radially outer end of the slot 31.

Figure 5:
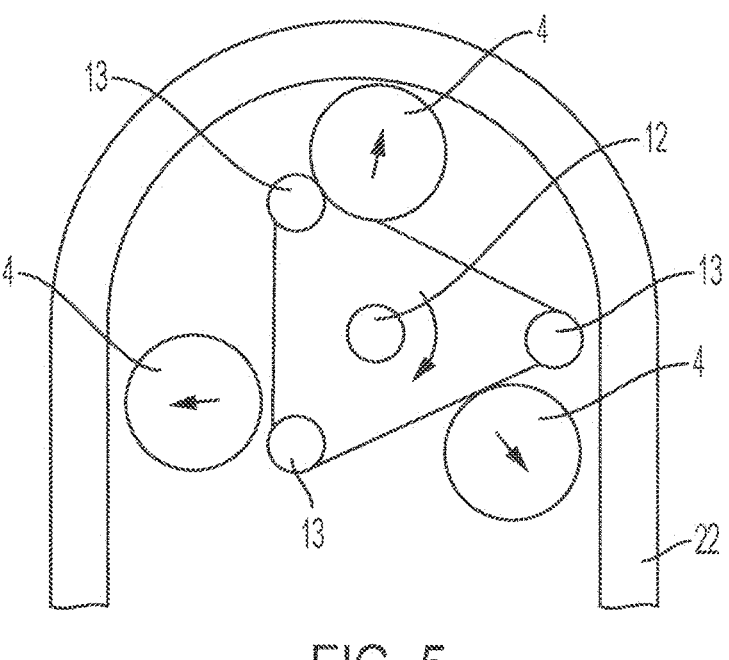
FIG. 5 is a schematic diagram of an alternate carrier, lobe and drive element in another illustrative embodiment.

FIGS. 1-3 show only one embodiment of a peristaltic pump 10 that includes one or more inventive features, and this embodiment should not be viewed as limiting inventive features in any way. For example, FIG. 5 shows a schematic view of another pump arrangement in which rotation of a carrier and/or lobe can cause the lobe to move radially outwardly. In addition, the FIG. 5 embodiment can be configured so that rotation of the carrier and/or lobe in either clockwise or counterclockwise directions can cause the lobe to move radially outwardly. In FIG. 5, a carrier 3 is not shown for clarity, but one or more lobes 4 are mounted to a carrier 3. The carrier 3 in FIG. 5 can be configured like that in FIG. 3, e.g., the lobes 4 can be configured as rollers mounted to a pair of carrier plates 3 that include slots 31 for the lobes 4. The slots 31 to which the lobes 4 are engaged on the carrier 3 can be configured like that in FIG. 3 or in other ways, such as a single, linear radially oriented slot, a slot having a "U" or "V" shape, and so on. A drive element 13 coupled for rotation by the drive motor 1 can be configured to contact a lobe 4 to drive the lobe 4 to rotate in clockwise and/or counterclockwise directions. Thus, the motor 1 can be configured with a drive element 13 to contact a lobe 4 and cause the lobe 4 and the carrier 3 to rotate. For example, the drive element 13 can include a drive roller mounted on the drive shaft 12 of a motor 1 and configured to contact the lobe 4 (e.g., which can be configured as a tube roller) to cause the lobe to rotate in the clockwise or counterclockwise direction about the drive axis 11 and to move radially outwardly. The lobe 4 can be mounted for rotation relative to the carrier 3 about an axis, e.g., the lobes 4 can be configured as tube rollers and mounted to rotate on the carrier about a tube roller axis. Similarly, the drive elements 13 can be configured as drive rollers configured for rotation about the drive axis and about a drive roller axis relative to the drive shaft 12. Each drive roller can contact a first tube roller 4 to cause the first tube roller 4 to rotate in the clockwise or counterclockwise direction and move radially outwardly. In some cases, the configuration in FIG. 5 can operate in both clockwise and counterclockwise directions. In such a case, each drive roller 13 can contact a first tube roller 4 for clockwise rotation and contact a second tube roller 4 for counterclockwise rotation. Accordingly, the pump can be reversible and operate to move fluid in two directions. Also, the drive elements 13 can be configured for positioning in a state such that the pump permits free flow through the pump conduit 22. For example, the drive elements 13 can be put out of contact with any lobe 4, and lobes 4 can move radially inwardly so that the pump conduit 22 is not occluded. The lobes 4 can move radially inwardly to permit flow in the pump conduit 22 based on resilience of the pump conduit 22 and/or a resilient element that retracts the lobes 4 radially inwardly and/or reversal of the drive element 13 direction.

Embodiments like that in FIG. 5 include another inventive feature, i.e., that a drive motor can be configured to contact a lobe to move the lobe radially outwardly to contact the flexible pump conduit and to rotate the lobe and carrier about a drive axis to cause the fluid movement in the flexible pump conduit. While embodiments are described above in which the FIG. 5 arrangement can be operated in both clockwise and counterclockwise directions, this is not required. Instead, arrangements like that in FIG. 5 may be configured to operate (or at least operate to move fluid) in only one rotational direction. For example, an arrangement like that in FIG. 5 can be configured to pump fluid when operated in a clockwise (or counterclockwise) direction, but to retract the lobes 4 to permit free flow through the pump conduit 22 when operated in the counterclockwise (or clockwise) direction. In such a case, a slot 31 having a single arcuate segment like that in FIG. 4 can be employed for each lobe 4.

Figure 6:
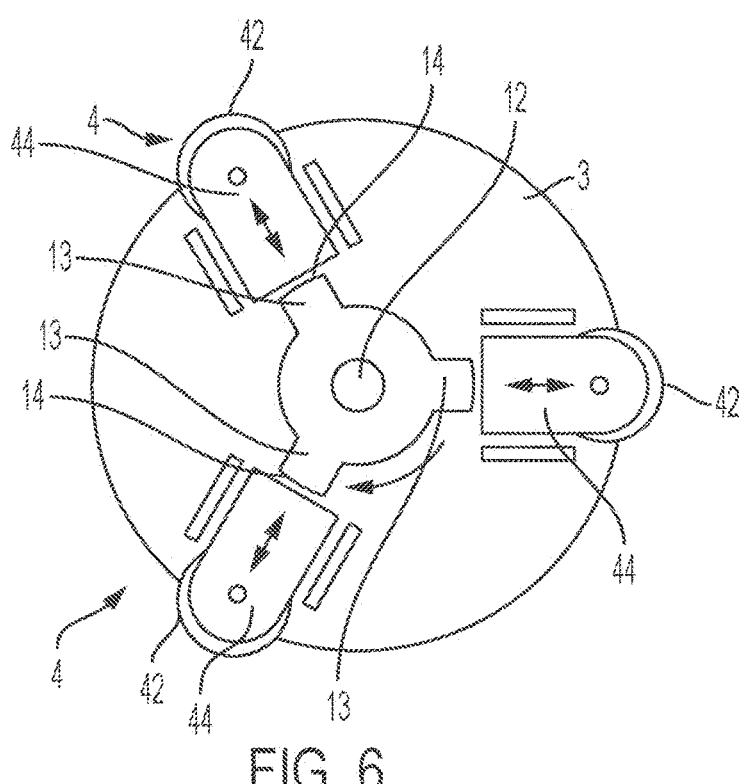
FIG. 6 is a carrier and lobe arrangement in which lobes are mounted on a respective carriage on a carrier.

FIG. 6 shows another embodiment in which a drive motor is configured to contact a lobe to move the lobe radially outwardly to contact the flexible pump conduit and to rotate the lobe and carrier about a drive axis to cause the fluid movement in the flexible pump conduit. In some cases, an arrangement like that in FIG. 6 can function to pump fluid only for rotation in one direction, e.g., when operated in a clockwise direction, but not when operated in the counterclockwise direction. For example, FIG. 6 shows an arrangement in which a drive shaft is configured to contact a lobe 4 to move the lobe radially outwardly and rotate the lobe 4 and carrier 3 in response to rotation of the drive shaft 12 in the clockwise direction about the drive axis. In some embodiments like that in FIG. 6, the drive shaft can include a lobe-engagement element 13 configured to contact and rotate relative to the lobe 4 to cause the lobe 4 to move radially outwardly. In some examples, the lobe-engagement element 13 includes a cam with cam surface 14 configured to contact the lobe 4, as shown in FIG. 6. While the cam surface 14 is configured to engage the lobe 4 and move the lobe 4 radially outwardly for clockwise rotation, it is not configured to do so for counterclockwise rotation. Clockwise rotation of the lobe-engagement elements 13 also causes the lobes 4 to rotate clockwise about the drive axis 11, thereby driving rotation of the carrier 3 as well.

In some embodiments, the lobe 4 can include a tube roller 42 pivotally mounted on a carriage 44 that is slidably mounted to the carrier 3. Each carriage 44 can ride in a radially oriented slot or guide so that the carriage 44 and tube roller 42 can move radially on the carrier 3, but engages the carrier 3 to cause the carrier 3 to rotate about the drive axis 11. The carriages 44 can be resiliently biased to move radially inwardly, e.g., so that when the lobe-engagement elements 13 disengage from the carriages 44, the carriages 44 move radially inwardly.

Features of this disclosure may be embodied as a method, e.g., a method of operating a pump according to embodiments and modes of operation described. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, "beverage" refers to a liquid substance intended for drinking that is formed when a liquid interacts with a beverage material, or a liquid that is dispensed without interacting with a beverage material. Thus, beverage refers to a liquid that is ready for consumption, e.g., is dispensed into a cup and ready for drinking, as well as a liquid that will undergo other processes or treatments, such as filtering or the addition of flavorings, creamer, sweeteners, another beverage, etc., before being consumed.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

The invention claimed is:

1. A peristaltic pump comprising:
   a housing defining a cavity configured to hold a flexible pump conduit;
   a carrier mounted in the cavity for rotation relative to the housing;
   a lobe mounted for rotation with the carrier and configured to contact and compress the flexible pump conduit against the housing to cause fluid movement in the flexible pump conduit, the lobe being mounted to the carrier for radial movement; and
   a drive motor configured to rotate the carrier and lobe in a first direction and a second direction opposite the first direction, wherein the carrier and lobe are configured to move the lobe from a radially retracted position to a radially extended position in response to rotation of the carrier and lobe by the drive motor in both the first direction and the second direction.

2. The pump of claim 1, wherein the carrier includes a slot and the lobe is configured to move radially outwardly along the slot.

3. The pump of claim 2, wherein the slot extends in a radial direction on the carrier.

4. The pump of claim 2, wherein the slot includes a pair of curved portions that meet at a junction and respectively extend from the junction in a radially outward direction.

5. The pump of claim 4, wherein the pair of curved portions form an "M" shape.

6. The pump of claim 2, wherein the drive motor is configured to rotate the carrier to cause the lobe to rotate with the carrier in the first and second directions.

7. The pump of claim 2, wherein the drive motor is configured to rotate the lobe to cause the carrier to rotate with the lobe in the first and second directions.

8. The pump of claim 2, wherein the lobe includes a pivot axis about which the lobe is rotatable relative to the carrier, and the pivot axis is configured to move along the slot.

9. The pump of claim 1, further comprising a drive element coupled for rotation by the drive motor, the drive element configured to contact the lobe to drive the lobe to rotate in the first and second directions.

10. The pump of claim 9, wherein the drive element includes a drive roller, and the lobe includes a tube roller mounted to the carrier, the drive roller configured to contact the tube roller to cause the tube roller to rotate in the first direction and move radially outwardly.

11. The pump of claim 10, wherein the drive roller is mounted for rotation about a drive axis, and wherein the drive roller is configured to contact the tube roller and cause the tube roller to rotate in the first direction about the drive axis in response to the drive roller being rotated in the first direction about the drive axis.

12. The pump of claim 11, wherein the drive roller is mounted for rotation about a drive roller axis that is spaced from the drive axis, and each tube roller is mounted for rotation relative to the carrier about a tube roller axis.

13. The pump of claim 9, wherein the drive element includes a plurality of drive rollers configured for rotation about a drive axis, and the lobe includes a plurality of tube rollers mounted for rotation with the carrier in the first and second directions about the drive axis, each drive roller configured to contact a first tube roller to cause the first tube roller to rotate in the first direction and move radially outwardly in response to rotation of the drive roller about the drive axis in the first direction, and configured to contact a second tube roller to cause the second tube roller to rotate in the second direction and move radially outwardly in response to rotation of the drive roller about the drive axis in the second direction.

14. The pump of claim 12, wherein each drive roller is mounted for rotation about a drive roller axis that is spaced from the drive axis, and each tube roller is mounted for rotation relative to the carrier about a tube roller axis.

15. The pump of claim 1, wherein the carrier includes first and second drive plates coupled to the drive motor, each of the first and second drive plates including first and second slots respectively, and
   wherein the lobe includes a roller having first and second opposed ends respectively engaged with the first and second slots and configured for movement along the first and second slots.

16. The pump of claim 15, wherein the first and second slots each include a pair of curved portions that meet at a junction and respectively extend from the junction in a radially outward direction.

17. A peristaltic pump comprising:

a housing defining a cavity configured to hold a flexible pump conduit;

a carrier mounted in the cavity for rotation relative to the housing;

a lobe mounted for rotation with the carrier and config- ured to contact and compress the flexible pump conduit against the housing to cause fluid movement in the flexible pump conduit, the lobe being mounted to the carrier for radial movement; and a drive motor configured to contact the lobe to move the lobe radially outwardly to contact the flexible pump conduit and to rotate the lobe and carrier about a drive axis to cause the fluid movement in the flexible pump conduit.

18. The pump of claim 17, wherein the drive motor includes a drive shaft configured to contact the lobe to move the lobe radially outwardly and rotate the lobe and carrier in response to rotation of the drive shaft about the drive axis.

19. The pump of claim 18, wherein the drive shaft includes a lobe-engagement element configured to contact and rotate relative to the lobe to cause the lobe to move radially outwardly.

20. The pump of claim 19, wherein the lobe-engagement element includes a drive roller configured to rotate about a drive roller axis that is spaced from the drive axis or a cam with cam surface configured to contact the lobe.

* * * * *